(12) United States Patent
Smoot et al.

(10) Patent No.: US 10,179,040 B2
(45) Date of Patent: Jan. 15, 2019

(54) ANIMATRONIC EYE WITH AN ELECTROMAGNETIC DRIVE AND FLUID SUSPENSION AND WITH VIDEO CAPABILITY

(71) Applicant: DISNEY ENTERPRISES, INC., Burbank, CA (US)

(72) Inventors: Lanny Starkes Smoot, Thousand Oaks, CA (US); Katherine May Bassett, Pasadena, CA (US); Marcus Hammond, Silverlake, CA (US)

(73) Assignee: DISNEY ENTERPRISES, INC., Burbank, CA (US)

( * ) Notice: Subject to any disclaimer, the term of this patent is extended or adjusted under 35 U.S.C. 154(b) by 836 days.

(21) Appl. No.: 14/230,873

(22) Filed: Mar. 31, 2014

(65) Prior Publication Data
US 2014/0214162 A1   Jul. 31, 2014

Related U.S. Application Data

(62) Division of application No. 12/560,778, filed on Sep. 16, 2009, now Pat. No. 8,715,033.

(51) Int. Cl.
*A61F 2/14* (2006.01)
*A63H 3/40* (2006.01)
(Continued)

(52) U.S. Cl.
CPC ............. *A61F 2/141* (2013.01); *A63H 3/40* (2013.01); *A63H 33/26* (2013.01); *G09B 23/30* (2013.01); *H04N 5/2251* (2013.01); *B33Y 80/00* (2014.12)

(58) Field of Classification Search
CPC ... A63H 3/38; A63H 3/40; A63H 3/42; A63H 33/26; A61F 2/14; A61F 2/141
See application file for complete search history.

(56) References Cited

U.S. PATENT DOCUMENTS 1,981,333 A * 11/1934 Schavoir ................ A63H 3/38
446/267
4,332,039 A * 6/1982 LaFuente ............... A61F 2/141
446/343
(Continued)

FOREIGN PATENT DOCUMENTS

JP        2007143919 A  *  6/2007

OTHER PUBLICATIONS

Translation of JP 2007143919 A.*
Refractive Index of some common Liquids, Solids and Gases. <http://www.engineeringtoolbox.com/refractive-index-d_1264.html>.*

*Primary Examiner* — Gene Kim
*Assistant Examiner* — Alyssa Hylinski
(74) *Attorney, Agent, or Firm* — Marsh Fischmann & Breyfogle LLP; Kent A. Lembke

(57) ABSTRACT

An animatronic eye with fluid suspension, electromagnetic drive, and video capability. The eye assembly includes a spherical, hollow outer shell that contains a suspension liquid. An inner sphere is positioned in the outer shell in the suspension liquid to be centrally floated at a distance away from the shell wall. The inner sphere includes painted portions providing a sclera and iris and includes an unpainted rear portion and front portion or pupil. The shell, liquid, and inner sphere are have matching indices of refraction such that interfaces between the components are not readily observed. A camera is provided adjacent a rear portion of the outer shell to receive light passing through the shell, liquid, and inner sphere. A drive assembly is provided including permanent magnets on the inner sphere that are driven by electromagnetic coils on the outer shell to provide frictionless yaw and pitch movements simulating eye movements.

15 Claims, 7 Drawing Sheets

(51) Int. Cl.
    *A63H 33/26*     (2006.01)
    *G09B 23/30*     (2006.01)
    *H04N 5/225*     (2006.01)
    *B33Y 80/00*     (2015.01)

(56) References Cited

U.S. PATENT DOCUMENTS

| | | |
|---|---|---|
| 5,900,923 A | 5/1999 | Prendergast et al. |
| 6,485,142 B1 | 11/2002 | Sheehy et al. |
| 6,803,738 B2 * | 10/2004 | Erten .................. H02K 41/031 310/103 |
| 6,879,082 B2 * | 4/2005 | Erten ...................... H02K 3/26 310/112 |
| 8,715,033 B2 * | 5/2014 | Smoot ..................... A61F 2/141 446/131 |
| 9,776,097 B2 * | 10/2017 | Smoot ..................... A61F 2/141 |
| 2002/0049023 A1 | 4/2002 | Simeray |
| 2008/0191827 A1 | 8/2008 | Hsiao et al. |
| 2009/0207239 A1 | 8/2009 | Warmerdam et al. |
| 2010/0041306 A1 | 2/2010 | Yang |

\* cited by examiner

US 10,179,040 B2

ANIMATRONIC EYE WITH AN ELECTROMAGNETIC DRIVE AND FLUID SUSPENSION AND WITH VIDEO CAPABILITY

CROSS-REFERENCE TO RELATED APPLICATIONS

This application is a divisional of U.S. patent application Ser. No. 12/560,778, filed on Sep. 16, 2009, which is incorporated herein by reference in its entirety.

BACKGROUND

1. Field of the Description

The present description relates, in general, to apparatus for simulating a human or human-like eye such as a robot or animatronic eye or a prosthetic eye, and, more particularly, to an animatronic or prosthetic eye assembly that utilizes fluid-suspension and is electromagnetically driven and that provides optical functions such as video capability.

2. Relevant Background

Animatronics are used widely in the entertainment industry to bring mechanized puppets, human and human-like figures, and characters to life. Animatronics are generally thought of as the use of electronics and robotics to make inanimate objects appear to be alive. Animatronics are used in moviemaking to provide realistic and lifelike action in front of the camera as well as in other entertainment settings such as in theme parks, e.g., to provide lifelike characters in a theme ride or a show. Animatronics are often used in situations where it may be too costly or dangerous for a live actor to provide a performance. Animatronics may be computer controlled or manually controlled with actuation of specific movements obtained with electric motors, pneumatic cylinders, hydraulic cylinders, cable driven mechanisms and the like that are chosen to suit the particular application including the show or ride setting or stage and the specific character parameters and movement requirements.

In the field of animatronics, there is a continuing demand to provide animatronic characters that better imitate humans and animals. Specifically, much of human and human-like character expression and communication is based on the eye including eye contact, eye movement, and gaze direction, and designers of robotic eyes attempt to mimic the subtle movements and appearance of the human eye to make animatronic figures more lifelike, believable, and engaging. To date, animatronic designers have not been able to accurately replicate human eye appearance and movement with challenges arising due to the need for rotation of the eye in a socket in a relatively rapid and smooth manner and also due to the relatively small form factor of the eye in an animatronic figure.

Many types of robotic or animatronic eyes have been created with a number of actuating mechanisms. To actuate or rotate the eye, a drive or actuating mechanism is provided adjacent the eye such as in the animatronic figure's head that includes external motors, hydraulic cylinders, gears, belts, pulleys, and other mechanical drive components to drive or move a spherical or eye-shaped orb. As a result, the eye assemblies require a large amount of external space for included moving parts, and space requirements have become a major issue as the eye itself is often dwarfed by the mechanical equipment used to move the eye up and down (e.g., tilt or pitch) and side-to-side (or yaw). The mechanical drive equipment has moving components external to and attached to the eye that needs mounting fixtures and space to freely move. In some cases, existing animatronic eye designs are somewhat unreliable and require significant amounts of maintenance or periodic replacement due, in part, to wear caused by friction of the moving parts including the eye within a socket device. To retrofit an eye assembly, the electromechanical, pneumatic, hydraulic, or other drive or eye-movement systems typically have be completely removed and replaced.

In some cases, animatronic eyes cannot perform at the speeds needed to simulate human eye movement. Movements may also differ from smooth human-like action when the drive has discontinuous or step-like movements, which decreases the realism of the eye. Additionally, many animatronic eye assemblies use a closed loop servo control including a need for a position or other feedback signal such as from optical, magnetic, potentiometer or other position sensing mechanisms. Further, the eye or eyeball's outer surfaces may rub against the seat or socket walls since it is difficult to provide a relatively frictionless support for a rotating sphere or orb, which may further slow its movement, cause wear on painted portions of the eyeball, or even prevent smooth pitch and yaw movements.

More recently, there has been a demand for video capability such as to assist in tele-operation of the animatronics or to provide vision-based interactivity (e.g., track a location of a person or other moving object relative to the animatronic figure and then operate the animatronic figure in response such as by moving the eyes or the whole head). Some animatronic eye assemblies have been provided with video functionality, with some implementations positioning a tiny video camera within the eyeball itself to move with the eyeball and with its lens at or providing the lens and/or pupil of the eye. However, this creates other problems because the camera power and signal lines may experience wear or be pinched by the movement of the eyeball or interfere with rotation of the eyeball as movement of the eyeball has to move or drag the cords that extend out the back wall of the eyeball.

Hence, there remains a need for improved designs for animatronic or robotic eye assemblies that better simulate the appearance and movements of the human eye or an animal's eye. Such designs may have a smaller form factor (or use less space for drive or movement mechanisms) when compared with existing systems, may be designed to better control maintenance demands, and may, at least in some cases, provide video capability.

SUMMARY OF THE INVENTION

The following description provides eye assemblies that are well-suited for animatronic figures or characters and also for human prosthetics. For example, an animatronic eye assembly may utilize fluid suspension for a rotatable/positionable eye (or spherical eyeball, orb, or the like) that is electromagnetically gimbaled or driven. The eye assembly may be compact in size such that it may readily be used to retrofit or replace prior animatronic eyes that relied on external moving parts to drive the eyeball's rotation. The animatronic eye assembly may include a solid, clear plastic inner sphere that is floated or suspended within a clear liquid, and the inner sphere or eyeball along with the suspension liquid may be contained or housed in a close-fitting, clear plastic outer shell or housing, which also may be generally spherical in shape. The floatation or suspension fluid may have its index of refraction matched to the plastics of the eyeball and of the outer shell/housing such that the entire eye appears to be a clear, solid plastic sphere even though it contains a rotatable eye or eyeball in its center. The outer shell, liquid, inner sphere or eyeball may act in conjunction as a lens or lens assembly of a tiny, stationary camera (e.g., a video camera) that can be mounted to the rear portion of the outer shell. The front (or exposed) portion of the inner sphere or eyeball may be painted to have a human eye appearance with a center sphere surface or portion left clear to allow light to be passed to the camera (e.g., to provide a pupil of the eyeball).

The eye assembly may utilize an electromagnetic drive in some embodiments, and, to this end, the inner clear sphere may have four permanent magnets or magnetic elements mounted to its top, bottom, and two sides at antipodal points about the equator or a great circle of the sphere. On the outer shell, four electromagnetic drives may be mounted so as to be associated with each of these inner sphere magnets (e.g., each electromagnetic drive is used to apply a magnetic or driving force upon one of the inner sphere magnets). The external drives may each include a pair of electromagnetic coils in which the coils are positioned adjacent and proximate to each other but, in some cases, on opposite sides of the equator (or a great circle of the outer shell that generally bisects the outer shell into a front and back shell portion or hemisphere) and with each drive equidistally spaced about the equator such that the four drives are located at 90 degree spacings and such that opposite electromagnetic drives include antipodal coils (e.g., coils on opposite sides of the outer shell with their center points being antipodal points on the outer shell/spherical housing). The external drive coils may be lay-flat, magnetic coils that may be selectively operated to generate magnetic fields (e.g., energize or drive antipodal coils concurrently) to yaw and tilt/pitch the inner sphere or eyeball. The design of the eye assembly has no external moving parts, which eases its installation in new, and in retrofit, animatronic applications.

The optical effects achieved by the eye assembly make it appear that the entire eye assembly is rotating (or at least that the outer shell is moving) within its mounting socket or location such as within an eye socket of an animatronic figure. Due to the magnification of the liquid in the outer shell, the inner eyeball or sphere appears to be as large as the entire outer shell, which means the eye assembly simulates a rotating eye even when the outer shell is locked into an eye socket and/or is under facial skin of an animatronic figure. The eye assembly with the shell, liquid, and inner sphere/eyeball (and other components in some cases) acting as a lens or lens assembly provides a foveal view that is automatically highlighted in the camera's image, and the spherical lens structure supports a relatively wide field of view even through the relatively small entrance portion of the inner sphere or eyeball (e.g., the pupil may be less than one third the front hemisphere of the inner sphere or orb such as 0.1 to 0.25 of the front hemisphere surface area). In some animatronic figures, two eye assemblies are provided that act to support stereo viewing while sharing the same electrical drive signal for objects at infinity while other arrangements provide eye assemblies that are arranged to be "toed-in" such as by using offset drive signals for their separate electromagnetic drive assemblies that may be derived from knowledge of an object's distance from the eye assemblies.

To provide a prosthetic implementation, the eye assembly may be separated into or include two parts: a hermetically sealed plastic eyeball and a remote electromagnetic drive including coils and control components. The sealed eyeball contained within a suspension fluid in a substantially clear outer shell or housing may be positioned within a human eye socket such as in a recipient that has one functioning eye. The drive assembly may be provided remotely such as within a frame of a set of glasses or otherwise attached/supported to the recipient's head near the skull and eye sockets. The eye assembly may be gimbled or driven magnetically through the skull such as by providing electromagnetic coils or a positionable permanent magnet in the eye glasses, and the motion of the prosthetic eye in the eye assembly may be controlled so as to match movement of the recipient/user's functioning eye such as based on an eye-tracker (e.g., camera with tracking software) that may also be built into or provided on the eyeglasses. The eye assembly is attractive for use as a prosthetic due to its form factor and lack of rotation of the outer shell within the recipient's eye socket (which may be undesirable due to discomfort and other issues associated with implanting prosthetics).

More particularly, an apparatus is provided for simulating an eye such as to provide an animatronic eye(s). The apparatus includes an outer shell with a thin wall that defines, with its inner surface, a substantially spherical inner void space and that has a substantially spherical outer surface. The outer shell has a front portion (e.g., front hemisphere or the like) and a rear portion (e.g., rear hemisphere or the like) that both transmit light with a first index of refraction (e.g., are substantially clear or at least highly transmissive of light as with most glasses and many plastics). The apparatus further includes a volume of flotation or suspension liquid contained within the inner void space of the outer shell, and the liquid transmits light with a first index of refraction substantially matched to the second index of refraction (e.g., within 10 percent or less of the same index value). The apparatus also includes an inner sphere with a solid body of material with a third index of refraction that substantially matches the first and second indices of refraction, and the inner sphere is positioned within the inner void space of the outer shell to float in the suspension liquid.

The apparatus further includes a camera, such as a video camera, with an image capturing device positioned adjacent or near the rear portion of the outer shell such that it receives light passing through the outer shell, the suspension liquid, and the inner sphere (e.g., these three components act as a single camera lens with the index of refraction matching causing only the front and back surfaces of the shell to have any optical value). The rear portion of the shell may include an opaque hemisphere with an opening formed therein and a spherical camera lens or lens element may be positioned over the opening to provide a liquid seal with an outer surface of the opaque hemisphere. This camera lens may be shaped to correct focusing of the camera such as to provide an overall spherical shape with the shell components and/or to cause the image capture device to focus on the front portion of the outer shell (and, typically, not on the inner sphere or the suspension liquid).

In some embodiments, the solid body and the wall of the outer shell may be formed of a substantially transparent plastic such as an acrylic. In practice, the suspension liquid may be chosen to have a specific gravity such that the inner sphere has neutral buoyancy whereby it floats in the center of the void space and liquid fills the space between the solid body and the inner surfaces of the outer shell wall (e.g., the body is maintained at a spaced apart distance from the shell). For example, when the body is a plastic (and may contain further weight-adding components such as permanent magnets), the liquid may be a mixture of glycerin and water such as ¾ glycerin and ¼ water or the like to achieve a desired buoyancy of the body and also, in some cases, to provide a desired viscosity so as to dampen movement of the body during quick rotation (e.g., to control movements solely on momentum or the like). In some cases, it is desirable that the inner sphere body has a diameter that is smaller than the thin wall's inner diameter but without excessive spacing such as by providing the body with an outer diameter that is at least 80 to 90 percent or more of the inner diameter of the shell (or such that a spacing is less than about 0.5 inches and more typically less than about 0.25 inches such as less than about 0.1 inches or the like).

The apparatus may further include an electromagnetic drive assembly that provides a set of magnetic elements (such as small permanent magnets) on the solid body of the inner sphere (such as two to four or more magnets spaced equidistally about a great circle of this sphere). The drive assembly may also include a like number of electromagnetic drive mechanisms positioned on or proximate to the outer surface of the outer shell, and these drive mechanisms are selectively operable to apply drive magnetic fields to the magnetic elements to provide yaw and pitch movements (concurrent or independent) to the solid body. Each of the drive mechanisms may also include a restoring permanent magnet that is positioned on or proximate to a great circle (or equator) of the outer shell to apply a restoring magnetic force on each of the magnetic elements on the inner sphere body to return/maintain the body in a predefined central/ neutral position in the inner void space of the outer shell (e.g., spaced apart from the wall with its center coinciding with a center of the sphere defined by the outer shell).

In one embodiment, the magnetic elements include four permanent magnets spaced 90 degrees apart about a great circle of the inner sphere body, and four electromagnetic drive mechanisms are provided on the outer shell near a great circle/equator of the shell's sphere. Each of these drive mechanisms includes a pair of electromagnetic coils that are positioned adjacent each other but on opposite sides of the great circle (e.g., mounted on opposite hemispheres of the outer shell). The coils are positioned such that pairs of the coils in opposite drives make up antipodal coil pairs (with an axis extending through their center points also extending through antipodal points of the outer shell sphere). The drive assembly is operable to concurrently operate antipodal pairs of the coils so as to apply an equal and opposite (or symmetric) magnetic drive force on the permanent magnets of the inner sphere body, whereby the inner sphere body may be caused to move through a range of yaw and pitch movements while remaining spaced apart from the wall of the outer shell.

DETAILED DESCRIPTION OF THE PREFERRED EMBODIMENTS

Figure 1:
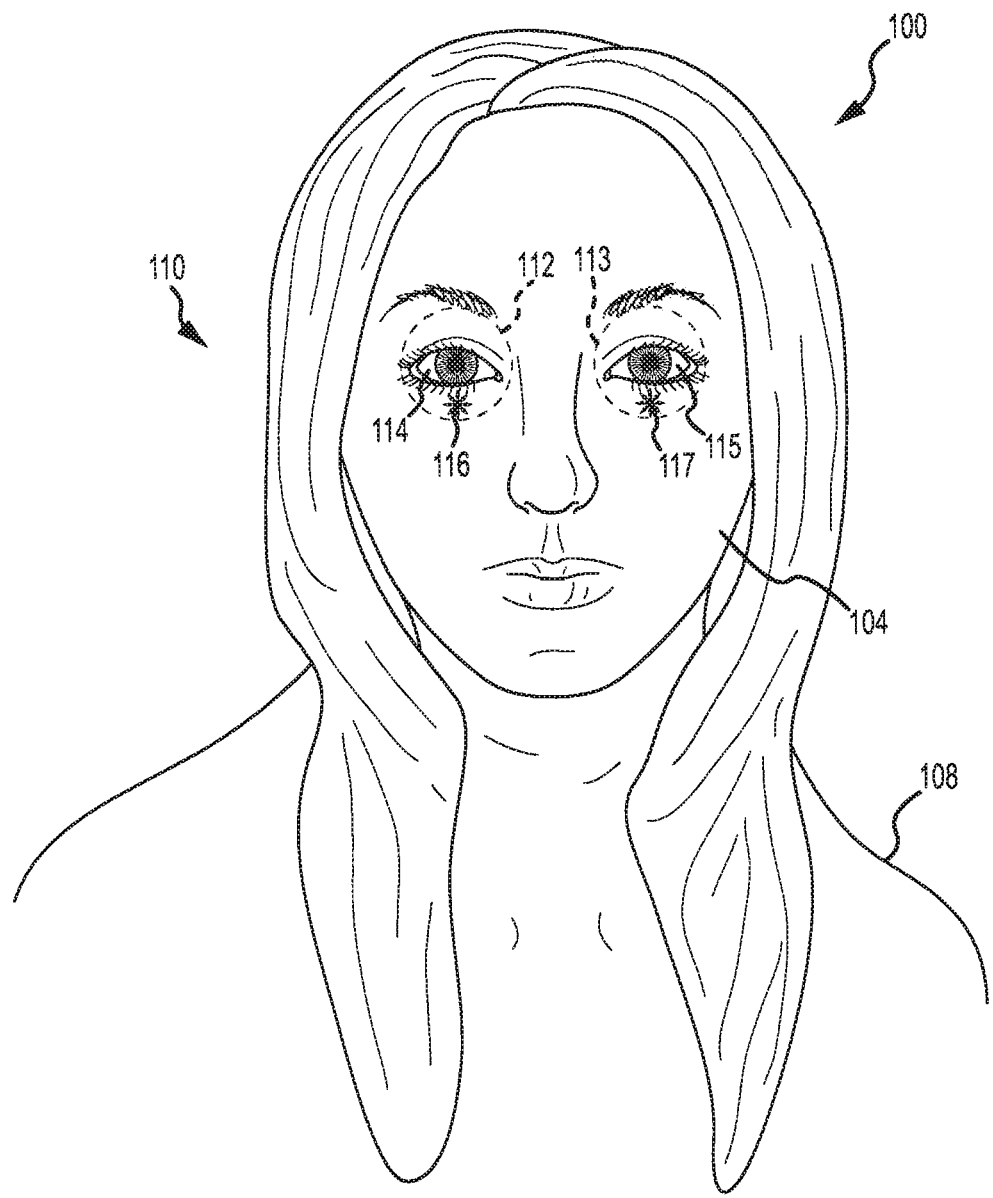
FIG. 1 illustrates a perspective view of an animatronic figure including an eye assembly that provides a pair of magnetically driven eyes with fluid suspension as described herein.

Briefly, embodiments described herein are directed to a compact, fluid-suspension, electromagnetically-gimbaled (or driven) eye that may be used in eye assemblies for animatronic figures as well as for human prosthetics. Each eye or eye assembly features extremely low operating power, a range of motion and saccade speeds that may exceed that of the human eye while providing an absence of frictional wear points (e.g., between the eyeball or inner sphere and an eye socket). The design of the eye assembly has no external moving parts, which eases its installation in new and retrofit animatronic applications.

The eye assembly may include a clear or substantially transparent outer shell that contains a suspension fluid and an inner orb or sphere (e.g., an eyeball). The inner sphere may be a solid plastic or similar material ball with a set of magnetic elements attached or embedded thereon. An electromagnetic drive assembly may be provided that includes a set of magnetic drive mechanisms or components attached to the outer shell and each magnetic drive mechanism may include two magnetic coils and a permanent magnet used for restoring the inner sphere to a neutral position within the outer shell. For prosthetic applications, the eye portion (e.g., the shell, liquid, and inner sphere) may be separated from the electromagnetic drive as a hermetically sealed portion that may be placed in the eye socket, and the drive may be provided as an extra-cranially-mounted magnetic drive or the like. By using a controller or driver to selectively energize opposite or antipodal pairs of the magnetic coils, the inner sphere may be caused to rotate away from the neutral position (e.g., by overcoming the restoring or retaining forces of a set of permanent magnets) as desired to simulate an eye's movements such as to follow an object passing by an animatronic figure's head, to move as would be expected with speech or other actions of an animatronic figure, and so on.

A video or other camera may be mounted on the rear, outer portion of the outer shell, and it may focus through the outer shell (or a lens thereon), through the suspension fluid, and through the inner sphere (which may be painted to take on the appearance of a human or other eye but leaving a rear port/window or viewing portion of the inner sphere as well as a front/entrance window or pupil that is unpainted or clear/transmissive to provide a path for light through the eye assembly). In other words, all or much of the eye assembly acts as a lens assembly for the camera, and, to support this function, the indices of refraction of the shell, suspension liquid, and inner sphere may be selected (e.g., matched or nearly correlated) to provide a unitary lens effect with a clear view through the entire structure (except for painted portions) from front to back, making a rear stationary camera possible, and the camera view is supported without a large entrance pupil and using a still camera even during rotation of the inner sphere or eyeball. Two eye assemblies may be used to support stereo viewing or imaging while they may share the same electrical drive signals from a controller/driver for viewing objects at infinity. Alternatively, the eyeball or inner spheres may be toed-in by using offset drive signals derived from a knowledge or calculation of object distances.

FIG. 1 illustrates an animatronic figure 100 with a head 104 supported upon a body 108 (which is only shown partially for convenience but not as a limitation). Significantly, the animatronic figure 100 includes an eye assembly 110 that may be implemented according to the following description (such as shown in FIGS. 2-6) to provide realistically moving eyes as well as an animatronic figure 100 with video capabilities. As shown in FIG. 1, the eye assembly 110 may include first and second fluid suspension, electromagnetically driven eyes 112, 113 that each includes an inner sphere or eyeball 114, 115 that may be driven through the use of magnetic forces to rotate in any direction as indicated with arrows 116, 117.

The number of eyes or eye devices 112, 113 is not limiting to the invention with some assemblies 110 including one, two, three, or more eye/eye devices that may be driven concurrently with the same or differing drive signals (e.g., to rotate similarly or independently) or driven independently with the same or differing drivers. Two eyes or eye devices 112, 113 are shown to indicate that an animatronic figure 100 may be provided with stereo video capabilities similar to a human by providing a video camera attached in each eye or eye device 112, 113 while other embodiments may only include one eye or eye device 112, 113 or one camera (e.g., only mount a video camera on an outer shell, for stationary mounting, of one of the two eyes 112, 113).

Figure 2:
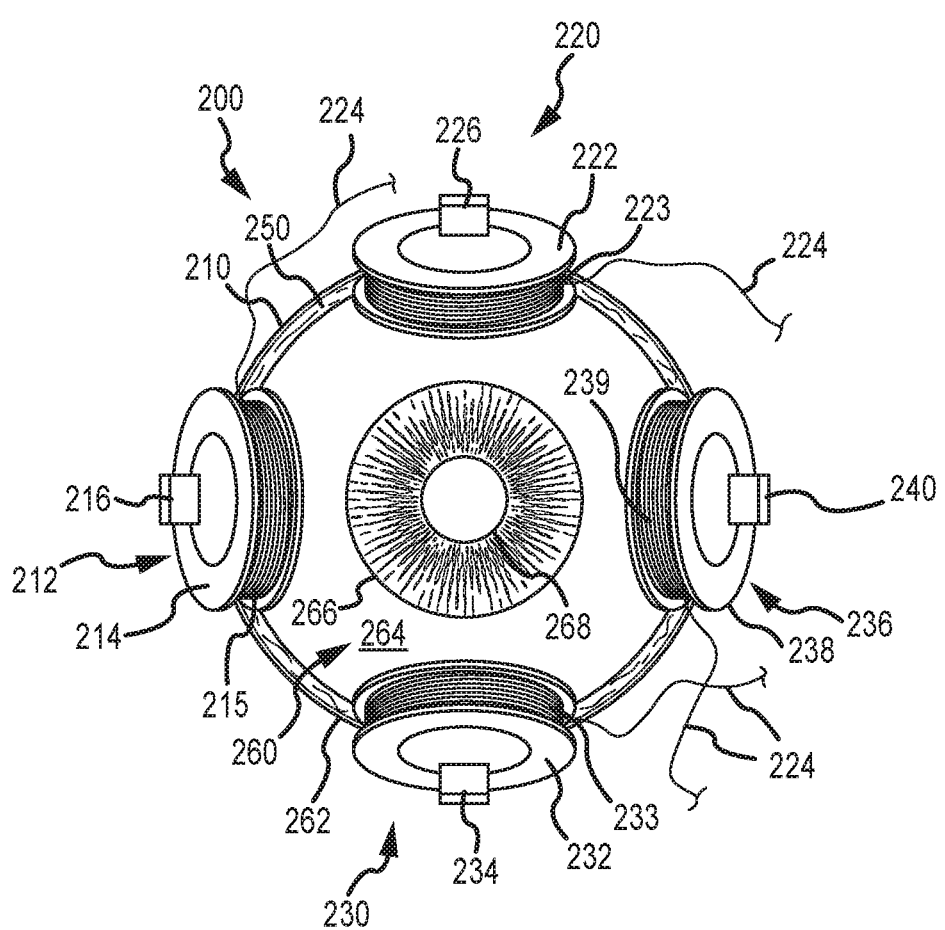
FIG. 2 is a front view of an animatronic eye assembly with fluid suspension, an electromagnetic drive, and video capability as may be used in the animatronic figure or character of FIG. 1.
Figure 3:
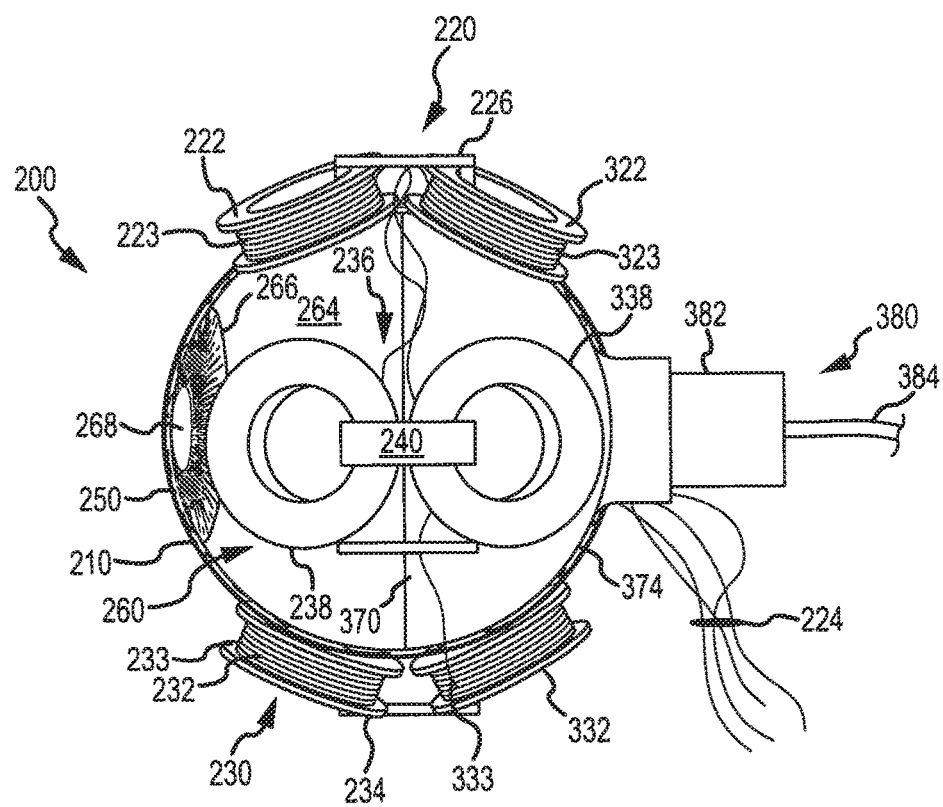
FIG. 3 is a side view of the animatronic eye assembly of FIG. 3 showing that each of the spaced apart magnetic drive mechanisms or components includes a pair of electromagnets adjacent to each other on opposite sides of the "equator" on an outer surface of a spherical eye housing (or container/outer shell)

The specific configuration of the eyes 112, 113 may be varied to practice the figure 100, but FIGS. 2 and 3 illustrate one useful eye or eye assembly 200 for providing the figure 100. As shown, the eye assembly includes an outer shell 210 that may be formed of an optically clear or substantially clear material such as a plastic (e.g., a high-grade acrylic or the like), a glass, a ceramic, or the like, and it is hollow with relatively thin outer walls that have an inner surface defining an inner volume or space of the assembly 200. The shell 210 may be formed of two or more parts such as a front and rear half or hemisphere and may be spherical or nearly spherical in its inner and outer shapes.

The assembly 200 includes an inner sphere or eyeball assembly 260 that is positioned within the outer shell 210 and is suspended within a volume of liquid 250 (or suspension liquid or fluid). The eyeball assembly 260 includes a spherical body 262 that may take the form of a solid ball or sphere formed of an optically clear or substantially transparent material such as a plastic (e.g., a high-grade acrylic or the like), a glass, a ceramic, or the like with outer dimensions that are less than the inner dimensions of the outer shell. In some embodiments of the assembly 200, the spherical body 262 has an outer diameter that is less than the inner diameter of the shell 210 by about 20 percent or less such that the body 262 and shell 210 are relatively close fitting with little spacing that is filled with the liquid 250 (e.g., the inner diameter of the shell 210 may be 1.5 inches while the outer diameter of the body 262 may be 1.25 inches or more such that a clearance or spacing of about 0.125 inches or less is provided between the body's surfaces and the inner surfaces of the shell with this void or suspension space filled with liquid 250).

The liquid 250 is chosen to have a specific gravity that allows it to support the weight of the ball 262 as well as to provide desired optical characteristics. Hence, it may be chosen to provide neutral buoyancy of the ball 262, e.g., to float ball 262 with its center of gravity coinciding with the center of the inner space/void defined by the inner surfaces of the outer shell 210. In this manner, the spacing between the inner surfaces of the shell 210 and outer surfaces of the body 262 may be substantially equal about the body 262. The liquid 250 also acts as a "lubricant" in the sense that there is no friction or physical contact between the body 262 and the shell 210 when the body 262 is rotated within the shell 210 (e.g., when the assembly 200 is operated as a spherical motor device). The optical characteristics may be chosen such that the liquid 250 has an index of refraction that substantially matches that of the shell 210 and/or the body 262 such that there is little or no refraction or diffraction at each material/component interface and the shell 210, liquid 250, and body 262 may generally act as a single lens or lens assembly and may create an effect where the body 262 and liquid 250 are nearly invisible to an observer.

Figure 6:
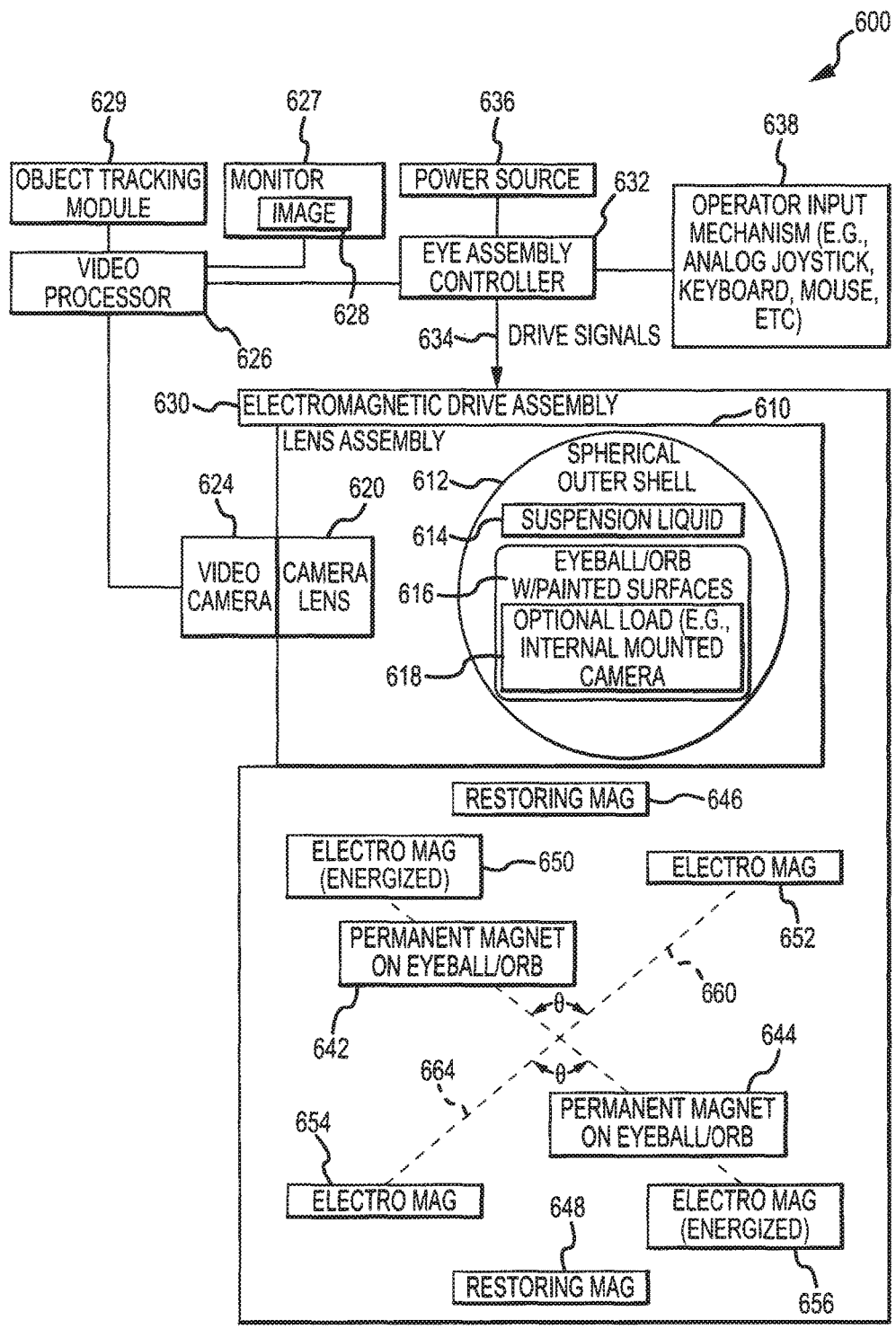
FIG. 6 is a functional block diagram of an animatronic eye assembly such as may be used to implement the assemblies shown in FIGS. 1-5.

The eye assembly 200 further includes an electromagnetic drive assembly with FIGS. 2 and 3 showing portions of this assembly that are used to control movement and positioning of the spherical body or eyeball 262 (e.g., with control/driver portions not shown in FIGS. 2 and 3 but discussed more with reference to FIG. 6). For example, to provide a control or drive functionality, the assembly 200 includes two drives or drive mechanisms 212, 236 that are used to drive, via control signals on wires/lines 224 that would be connected to a controller/driver (not shown), the eyeball or inner sphere assembly 260 by defining yaw or side-to-side movements. Further, the assembly 200 includes two drives or drive mechanisms 220, 230 that are used to drive the eyeball or inner sphere assembly 260 by defining pitch or tilt movements of the eyeball 262. Each of the drives or drive mechanisms 212, 220, 230, 236 include a pair of magnetic coils with coils 214, 222, 322, 238, 338, 232, 332 being shown as flat-laying coils wrapped with wire 215, 223, 323, 239, 339, 233, 333 (which is driven by input lines 224 that are linked to a controller/driver (not shown)).

Within each drive 212, 220, 230, 236, the magnetic coils are spaced on the outer surface of the shell 210 so as to be adjacent each other but on opposite sides of a great circle (or the equator) of the spherical shell 210. In this way, opposite pairs of the magnetic coils may be thought of as antipodal coils in the drive assembly that may be concurrently operated to drive the inner sphere body 262 to rotate through a range of yaw and pitch angles (independently or concurrently to define movement/rotation of the body 262 in shell 210). For example, axes extending through antipodal pairs of the coils may define a range of motion of about 15 to 30 degrees with 20 degrees being used in some implementations to define yaw and pitch movement ranges. Specifically, coils 222 and 332 may be one pair of antipodal coils that drive the ball 262 in the pitch direction while coils 232 and 322 may define the other pitch antipodal coil pair.

Although not shown in FIGS. 2 and 3, the eyeball assembly 260 would include a set of magnetic elements (e.g., permanent magnets on its outer surface or the like) that correspond in number and position to the drives 212, 220, 230, 236 (e.g., 4 permanent magnets may be embedded in the outer surface of the ball/body 262 at 90 degree spacings about a great circle or the equator of the body 262). By concurrently applying equal drive signals to either of (or both of) these antipodal pairs, the eyeball 262 may be caused to pitch or tilt forward or backward, and adding driving forces in the yaw drives 212, 236 may be used to cause the eyeball 262 to yaw or move side-to-side to provide a full (or desired amount of movement).

To return the eyeball or inner sphere 262 to a neutral position (as shown in the figures), each of the drives 212, 220, 230, 236 may further include a restoring magnet 216, 226, 234, 240. In one embodiment, the magnets 216, 226, 234, 240 are permanent magnets extending across the equator/great circle between (or overlapping) the adjacent coils (such as magnet 226 extending over/between coils 222 and 322) such that when no (or little) power is applied to the drives 212, 220, 230, 236 the magnetic force (e.g., an attractive force) provided by restoring magnets 216, 226, 234, 240 acts to cause the eyeball 262 to rotate to the neutral position with the inner sphere-mounted magnetic elements generally positioned between the drive coil pairs of each drive 212, 220, 230, 236 or adjacent the restoring magnetic 216, 226, 234, 240. This provides a power saving measure or function for assembly 200 in which the eyeball 262 is returned to and maintained at a desired position (which may or may not be a centered or straight-ahead gaze line as shown) without application of additional or ongoing power.

The eyeball or inner sphere body 262 may be colored or have its outer surface colored to achieve a desired optical effect and to simulate a human or other eye. For example, as shown, the front portion or hemisphere may include a portion that is white in color as shown with a colored iris portion 266 in its center. Further, to provide a direct light path, a clear pupil or entrance window/section 268 may be provided in the center of the iris portion 266. A rear portion or hemisphere 370 of the spherical body 262 may be made opaque to light such as with a blue or black coloring (as this portion is not visible when the assembly 200 is placed and used in an animatronic figure), and the light path is provided by leaving a viewing section or rear window/port 374 in the rear portion or hemisphere 370 free from coloring/paint.

To provide video capability, a video assembly 380 may be provided in assembly 200 and attached to the outer shell 210. As shown, a video camera or image capture device 382 is attached to the container or shell 210 with its lens (or a lens portion of the shell 210 as discussed in reference to FIGS. 4 and 5) coinciding with the clear or transparent window/port 374 of the surface of shell 210. The video camera 382 is rigidly attached to the shell 210 and not (in this case) the spherical body 262 such that the camera 382 is stationary or immobile during rotation or driving of the eyeball or body 262 with the electromagnetic drive assembly. Image signals/data may be transferred from the camera 382 to other components (such as monitoring or display equipment, object recognition and/or tracking software modules that may be used to control the movement of the eyeball 262, and the like) of the assembly 200 via line(s) 384 extending outward from camera 382.

From the front and side views of the assembly 200 and the above description, it will be understood that the eye assembly 200 uses a combination of liquid suspension and a compact electromagnetic drive to provide a selectively positionable eyeball 262 that accurately simulates human and other eyes. The eye assembly uses a sphere-in-a-sphere magnification illusion to good effect as even though the inner sphere or eyeball 262 is smaller than the inner dimensions of the outer sphere/shell 210, the overall effect when the assembly is viewed by a user or observer is that the eyeball or sphere 262 is exactly the diameter of the shell (or that there is a one piece construction such that the liquid 250 is invisible as is the floating eyeball 262). Because of this illusion, the entire eye may be caused to appear to rotate when the inner sphere or eyeball 262 is rotated within the liquid by magnetic driving forces while the outer surface of the shell 210 remains fixed in its mountings (such as within an animatronic figure's head/skull frame).

One feature of the eye assemblies described herein is that the outside of the eye does not move, e.g., the outer shell does not move relative to its mounting or support structure. Specifically, embodiments may have a stationary transparent housing or shell that is spherical (or generally so at least in its inner void space defined by the inner surfaces of its walls), and a transparent eyeball or inner sphere is floated in a suspension fluid or liquid within this shell. The shell and sphere's indices of refraction are matched to each other and to the floatation or suspension liquid, and, then, the structure formed by these three components, with the internal and moving/movable eyeball/sphere, make up a simple optical system or lens. Essentially, these components provide a transparent sphere or spherical lens with a single index of refraction. To provide a video or image capturing capability (or to make the eye assembly "see"), a video camera or other image capture device may be placed behind it and directed to receive light that passes through these three components or the spherical lens/optical system, e.g., use these components as the or a lens of the camera or image capture device. The camera may be stationary in this case such as by mounting it on or near the outer shell.

Figure 4:
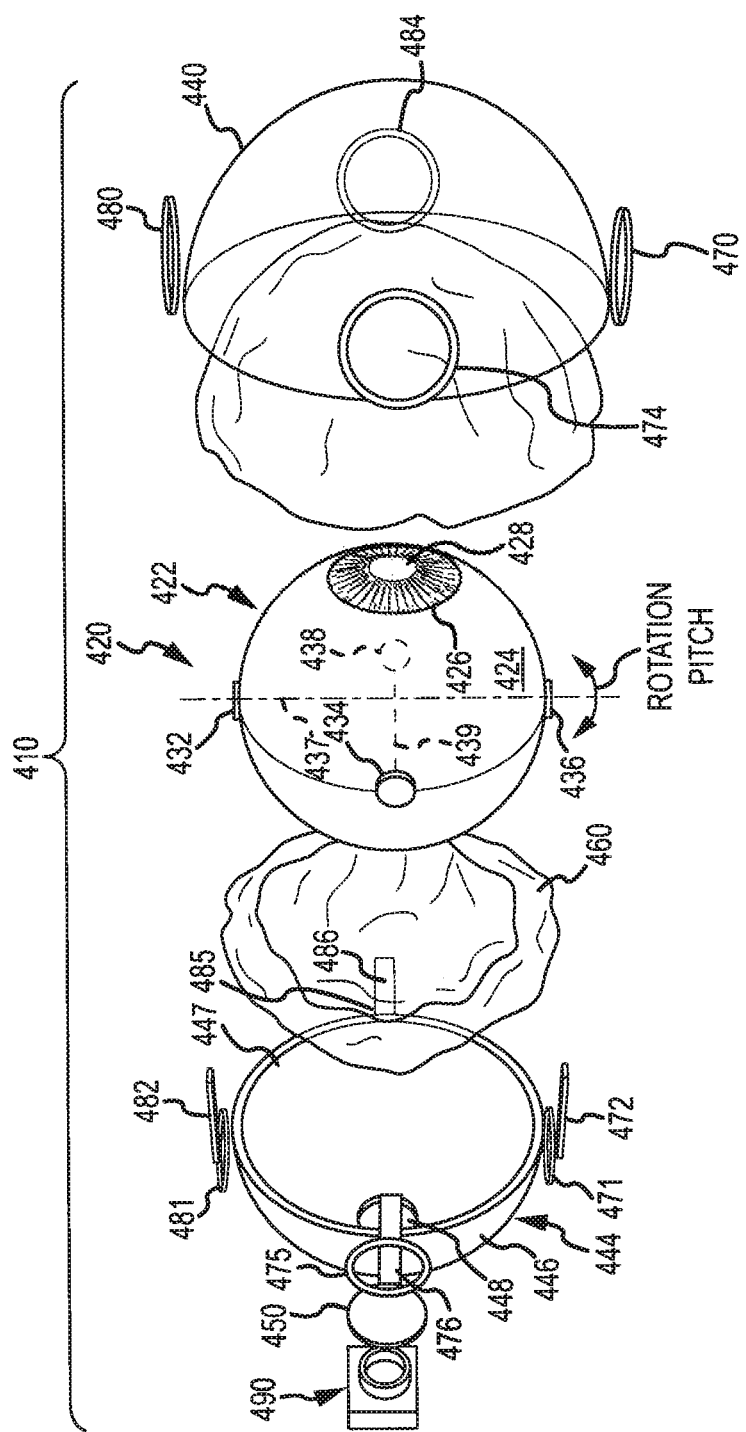
FIGS. 4 and 5 are exploded front and back views of an animatronic eye assembly as described herein and as may be used in animatronic figures as shown in FIG. 1.
Figure 5:
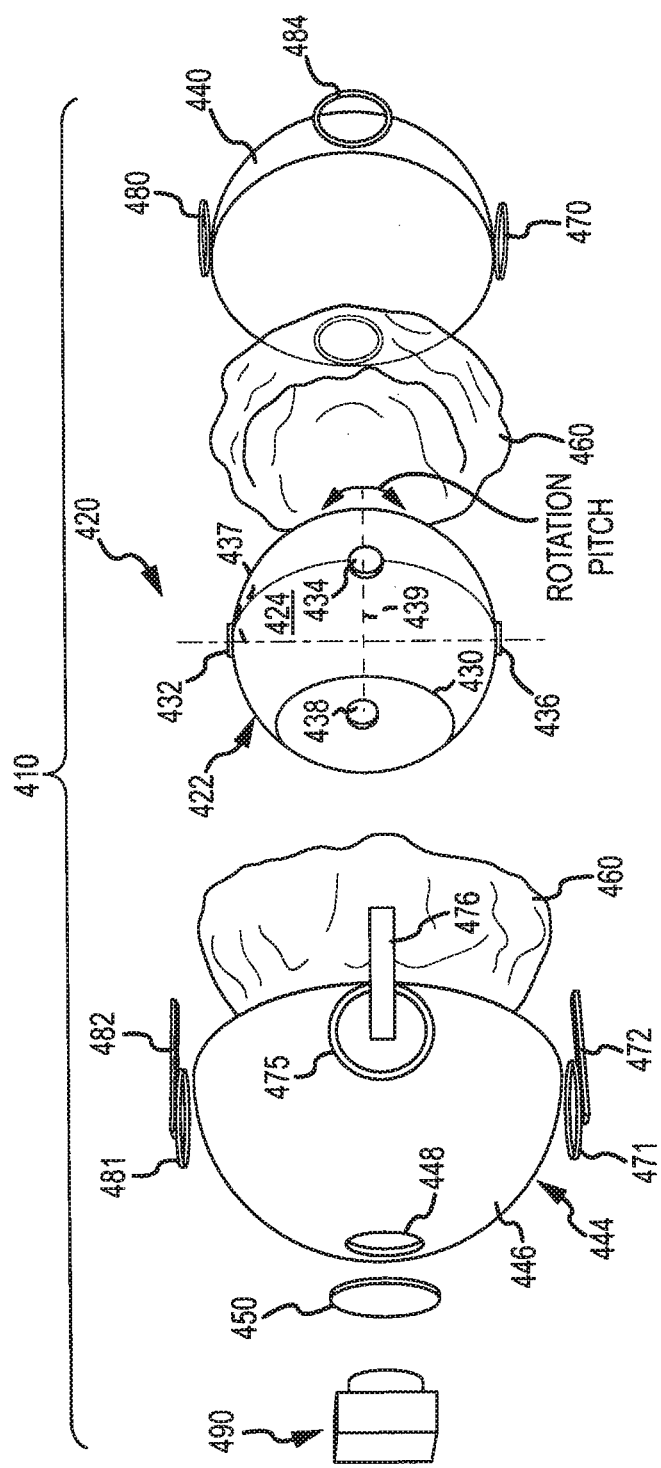

In order to create a believable organic eye, a realistic pupil, iris, and sclera may be provided so as to be visible from the front outside of the eye assembly. However, to achieve this effect and not interfere with a camera's optical path is not a trivial design challenge as the inventors pursued a number of approaches to achieve useful results (such as with the assemblies shown in FIGS. 2-5). FIGS. 4 and 5 illustrate exploded front and back views, respectively, of an eye assembly (or portion thereof) 410 according to one embodiment that was designed to facilitate manufacture and assembly as well as provide the drive and optical functions described throughout this description.

As shown, the assembly 410 includes an inner sphere or eyeball assembly 420 that includes a body 422 that may be formed as a solid ball or sphere from a clear or substantially transparent material such as plastic or glass. To simulate an eye while not interfering undesirably with an optical path for a camera 490, the body 422 has a first surface or spherical portion 424 that is painted with an exterior white layer to provide a sclera of the assembly 420. Next, a second surface or spherical portion 426 is painted a color (such as blue, brown, or the like) to provide an iris of the assembly 420. A "pupil" is provide in assembly as shown at 428 by providing a clear or unpainted third surface or spherical portion in the center of the iris or second surface 426 through which light may be received or enter the ball 422 (e.g., provide a port or window for light to pass). The optical path through the eyeball or spherical body 422 is further defined by a fourth surface or spherical portion 430 of the body 422 that is also left clear or unpainted and, which, may be larger than the pupil portion 428 but at least as large as the input to the camera 490 (e.g., at least as large as rear port/window 448 in a rear half/hemisphere 444 of the outer shell).

To allow remote/no contact driving of the sphere 422 using magnetic fields, the eyeball assembly 420 includes a set or number of magnetic elements 432, 434, 436, 438 attached to or embedded within the sphere 422. For example, the elements 432, 434, 436, 438 may each be a permanent button or disk magnet embedded into the outer surface of the spherical body 422 (e.g., to be flush or receded with the surface of sphere 422 or to extend out some small distance less than the expected separation distance between the sphere 422 and the inner surfaces of shell formed of halves/hemispherical elements 440, 444). The elements 432, 434, 436, 438 may be positioned about a great circle of the spherical body 432 and typically with equal spacing (or equidistally spaced) such as at 90 degree spacings about the great circle of the spherical body 422 when four magnet elements are utilized as shown (or at 120 degree spacings if 3 elements are used and so on when other numbers are used). Either magnetic pole may be exposed with the opposite being provided by the driving coil when attractive forces are used to drive the eyeball 422 in the assembly 410. As shown, an axis 437 extends between the top and bottom magnetic elements 432, 436 indicating, in this case, these are positioned at antipodal points on the sphere's surface and in use, rotation about this axis 437 may be considered yaw rotation or movement, $Rotation_{yaw}$. Similarly, an axis 439 extends between the two side magnetic elements 434, 438 showing these are also positioned on antipodal points of sphere 422 and when the eyeball 422 is caused to rotate about this axis 439 it may be thought of as having tilt or pitch movement or rotation, $Rotation_{pitch}$.

The eyeball or inner sphere 422 is rotated without friction in assembly 410. This is achieved in part by providing fluid suspension of the sphere 420 and in part by driving the rotation/movement using an electromagnet drive assembly. The fluid suspension is provided by a volume of liquid 460 that extends about and supports the sphere 422 such that it typically does not contact the inner surface of shell parts 440, 444 even as it is rotated or moved (e.g., which may be achieved by applying equal forces using antipodal pairs of drive magnet coils).

The assembly 410 further includes an outer housing or shell that is provided by a first or front portion or hemisphere 440 and a second or rear portion or hemisphere 444. In this embodiment, the front portion 440 of the outer shell is formed of a clear or substantially transparent material and is left unadorned to provide an open optical path to the eyeball or sphere 422. The rear portion 444 in contrast may be formed of more opaque materials and has an exterior surface 446 that may be painted (blue or other color or left the color provided via manufacturing) to provide a desired outer appearance of the eye while the inner surface 447 is painted a dark color (or left the color provided via manufacturing) such as black to limit the ability of an observer of the eye assembly 410 to see through the eye and to limit undesired reflections or transmittance of light. The rear portion 444 includes a port or opening 448 that is left unpainted in some cases or as shown is formed by removing the material (such as a plastic) used to form shell portion 444. Then, a camera lens 450 is attached over the opening or port 448 (e.g., an arcuate partial sphere formed of transparent plastic or the like may be sealably attached about the periphery of hole/opening 448. When assembled, the optical path of assembly 410 extends through the camera lens 450, the port or opening 448, a layer of liquid 460, the eyeball or sphere 422 (through portion 430 through the body thickness and then through the pupil 428), another layer or thickness of liquid 460, and then the front portion or hemisphere 440 of the outer shell. The assembly 410 further includes a video camera 490 such as a charge-coupled device (CCD) or the like that is affixed to the lens 450 or shell portion 444 or the like so as to be stationary even when the eyeball or sphere 422 is rotated.

The electromagnetic drive assembly is provided in eye assembly 410 with the inclusion of a top drive (shown as including coils 480, 481 and restoring magnet 482), a bottom drive (shown as including coils 470, 471 and restoring magnet 472), a first side drive (shown as including coils 474, 475 and restoring magnet 476), and a second side drive (shown as including 484, 485 and restoring magnet 486). As shown, each drive mechanism includes a pair of coils that are spaced adjacent to each other but on opposite sides of a great circle of the outer shell, e.g., one coil of each pair is attached to the front portion or hemisphere 440 and one coil of each pair is attached to the rear portion or hemisphere 444. Further, these coils are arranged on antipodal points such that a coil in another drive mechanism is on an opposite side of the outer shell (e.g., coil 480 is an antipodal coil to coil 471 while coil 481 is an antipodal coil to coil 470). In practice, for example, application of drive signal on coils 480 and 471 that is adequately strong to overcome the restoring forces of magnets 472, 476, 482, 486 will cause the eyeball or inner sphere 422 to pitch or tilt forward, $Rotation_{pitch}$, such as forward 10 to 20 degrees or more relative to vertical. Selective or concurrent driving of other ones of the antipodal pairs of the coils may be used to provide full motion of the eyeball 422 in the shell formed by halves 440, 444.

The arrangement of assembly 410 shown in FIGS. 4 and 5 was selected in part to suit a particular manufacturing method but, of course, a wide variety of other manufacturing techniques may be used, which may drive a somewhat different design such as elimination of the hole 448 and lens 450 when the shell portion 444 is formed of clear material similar to shell portion 440. In the illustrated assembly 410, the inventors determined that rather than using all transparent parts it may be more precise and reproducible to use a mix of clear and stereo-lithographically-produced (or otherwise provided) opaque hemispherical parts. Specifically, the front half 440 of the outer shell may be a hemisphere of transparent acrylic or other material and is left clear while the rear/back half 444 of the outer shell may be substantially a hemisphere but be opaque.

Since the front shell portion 440 provides the front of the camera's lens, the portion 440 typically will be manufactured to be optically smooth and as near as practical to an accurately shaped, hemispherical shell. For example, mold marks and aberrations may be controlled by using vacuum pulling with thermoplastic acrylic or the like at high temperatures into a hemispherical mold and terminating the pull just before the plastic or acrylic makes contact with the mold. This process may result in a shape that is slightly less than a full hemisphere, and this small deformation may be compensated for by fitting this piece or shell portion 440 into a back shell that is formed to be more-than-hemispherical (e.g., using precision stereo-lithography to form a greater than hemispherical shape in back shell portion 444), whereby the overall result of the shell is a hollow shell that is substantially spherical in shape.

In a manner similar to the human eye, the assembly 410 leaves or provides a pupil-sized clear area (e.g., one fourth or less of the sphere/ball 422 area) at the front of the solid transparent inner sphere 422 as shown at 428. The remainder of the front of the inner sphere 422 may be made opaque with a layer of black paint that may then be painted as desired to provide a white sclera 424 and a colorful iris 426. A relatively large part or portion 430 (such as one fourth or more of the sphere/ball 422 area) is left transparent to provide a clear view or optical path for the camera 490 through the sphere 422 even when the eyeball/sphere 422 is rotated. The inside 447 of the back shell half or portion 444 may be painted black, and a centrally located, small hole 448 may be cut or formed into the shell half 444. The hole or opening 444 may be filled in or covered with a spherical section cut, camera lens 450 as may be formed by cutting it from a transparent hemisphere the same diameter as the front hemisphere or shell portion 440 (or slightly larger or smaller in spherical diameter to achieve a desired focus or optical effect with the overall lens assembly or spherical lens provided by the assembly 410). The video camera 490 provided at the back of the eye assembly 410 adjacent the lens focus correction piece or camera lens 450 may be selected to be physically small (such as with a diameter of less than about 0.5 inches and more typically less than about 0.3 inches) and, thus, to work well with only a small sized hole 448 to pass light to its CCD or other image detection device/portion.

The space between the inner sphere 422 and outer shell formed of halves 440, 444 is filled with a suspension liquid 460. The liquid may serve at least three purposes including at least roughly matching the index of refraction of the sphere 422 and shells 440, 444 (or lens 450) so as to make all internal interfaces optically disappear or not be readily visible to an observer and/or to camera 490. The liquid 490 may also act to match the average specific gravity of the inner sphere 422 (including its small embedded magnets 432, 434, 436, 438) to render the internal sphere 422 neutrally buoyant so as to prevent (or limit) frictional rubbing on the top, bottom, and sides of the outer shell halves 440, 444 by sphere 422. Additionally, the suspension fluid 460 may be chosen so as to have a viscosity that provides a damping force on the rotation of the inner sphere 422, whereby over-spin during rapid eyeball 422 movements is better controlled (e.g., to provide a selectable, tunable amount of resistance to eye movement and to control momentum of the rotating eyeball 422). In one embodiment, the ball 422, shell portion 440, and camera lens 450 are formed of a substantially transparent acrylic, and, in this case, the suspension fluid 460 is made up of a mixture of approximately ¾ glycerin (e.g., 90 to 99 or more percent pure glycerol or glycerin) and ¼ water to achieve these purposes of the suspension fluid.

The structures or assemblies described above use a solid internal sphere and a transparent outer shell to provide a clear view through the eye to a camera or other image detection device even during pupil (and eyeball/inner sphere) rotation. This is due in part to the fact that the pupil is located behind the front surface of the entire eyeball lens (e.g., behind the liquid and front half of the outer shell). Hence, the pupil is out of the camera focus and acts as or similar to an aperture stop. At the extremes of eye movement (such as up to +/−20 degrees or more of yaw and/or pitch movement), the overall light available to the camera decreases because of the oblique position of the iris, but the automatic gain control (AGC) of the camera may compensate for this. Also, the depth of field increases somewhat at the extreme positions of the eyeball/inner sphere, and some spherical aberration may become apparent, which may make it desirable to limit the range of yaw and pitch movements (e.g., to about plus/minus 20 degrees or less or the like).

FIG. 6 illustrates a functional block diagram of an eye assembly 600 of one embodiment that is useful for showing control (and other) features that may be used to implement the assemblies shown in FIGS. 1-5 and 7. The assembly 600 includes a lens assembly 610 that is made up of a spherical outer shell 612 that is typically formed with a transparent or substantially clear thin wall (such as a two part shell of transparent glass, plastic, or the like). A suspension liquid 614 is provided within this shell 612 that has an index of refraction matching or selected based on the index of refraction of the shell 612 (as well as to provide a specific gravity to provide neutral buoyancy of the orb 616 and to provide a desired viscosity to control travel of the orb 616). The lens assembly further includes an eyeball or orb with or without painted surfaces such as a solid sphere of transparent or substantially clear material with an index of refraction matching or selected based on the index of refraction of the liquid 614 (such that interfaces between the orb 616 and liquid 614 are not readily visible to an observer or to the camera 624). The orb 616 may also include an optional load 618 within its interior when the orb 616 is hollow (such as an internally mounted camera in place or in addition to camera 624) or on an external surface. The lens assembly 610 may also include a camera lens 620 attached to the exterior surface of the shell 612 (such as to cover a hole cut into the shell 612 when a rear portion is opaque or so as to correct/adjust focusing through lens assembly 610). The camera lens 620 may also be provided with or connected to the video camera 624.

The image data from video or other camera 624 are transferred to a video processor 626 for processing such as for display on monitor or display device 627 as shown at 628. The processor 626 may also run an object tracking module 629 to process the image data to determine or recognize an object in the image data and/or track a location of the object relative to the lens assembly 610, and this information may be provided to an eye assembly controller 632 for use in positioning the lens assembly 610 (e.g., to cause the eye assembly 610 to rotate to follow or move a gaze direction based on an object's location or the like). The assembly 600 uses the eye assembly controller 632 to generate drive signals 634 that are used by the electromagnet drive assembly 630 to rotate/position the lens assembly 610 and, more accurately, to rotate/position the eyeball/orb 616 within the shell 612 (which is typically stationary and mounted to a frame such as within an animatronic figure). A power source 636 may be used by the controller 632 to generate a signal 634 (e.g., a voltage signal or the like) and the operation of controller 632 may follow a saved program (e.g., operate the drive assembly 630 based on code/instructions stored in memory of assembly 600 not shown) and/or be based on data from tracking module 629 and/or be based on user input mechanism 638 (e.g., a user may input control data via an analogy joystick a keyboard, a mouse, a touchscreen, or other input device).

As shown, the drive assembly 630 includes permanent magnets 642, 644 that are mounted or provided on or in the eyeball or inner sphere 616. For example, two, three, four, or more rare earth or other permanent magnets may be embedded or attached to the eyeball or sphere 616 such as a number of magnets equally spaced apart about the surface such as on a great circle of the sphere 616. The drive assembly 630 also includes a number of restoring magnets 646, 648 that are provided to apply a continuous magnetic field upon the permanent magnets 642, 644 of the eyeball 616 to return and maintain the orb 616 at a center or neutral position (e.g., proximate to the magnets 646, 648), and, as such, the restoring magnets 646, 648 may have a like number as the eyeball/orb magnets 642, 644 and a similar spacing/position on the outer shell 612 as the magnets 642, 644 (each may be on a great circle and spaced apart about 90 degrees when four magnets are used). Hence, when no (or minimal energy) drive signals 634 are provided, the restoring magnets 646, 648 apply magnetic forces upon the eyeball/orb 616 that causes it to return and/or remain in a predefined center or neutral position within the shell 616 (e.g., spaced apart from the shell 612 and with a pupil gazing or directed generally straight outward or another useful position for the application).

The drive assembly 630 provides an electromagnetic-based drive and, to this end, includes a plurality of electromagnets 650, 652, 654, 656 positioned on or near (close enough to apply adequate magnetic forces on the magnets 642, 644) the spherical outer shell 612. Typically, side-by-side or paired electromagnets 650, 652 are positioned adjacent to each other but with a center of their coils spaced apart and on opposite hemispheres of the shell 612. In this manner, the restoring magnets 646, 648 may be used to try to retain the magnets 642, 644 in a plane passing through or near a great circle (e.g., equator) of the outer shell 612 while selective energization of antipodal pairs of the electromagnets 650 and 656 or 652, 654 causes the magnets 642, 644 to be displaced from the neutral position. As shown, axes 660, 664 extend through antipodal points on the spherical shell 612 coinciding generally with centers of coils 650, 656 and 652, 654. The angle, θ, defined by these intersecting axes 660, 664 defines a range of movement of the eyeball 616 relative to a neutral position (e.g., when a plane passes through the restoring magnets 646, 648 as well as the permanent magnets 642, 644), and this range may be plus/minus 15 to 30 degrees such as plus/minus 20 degrees in one embodiment. As shown, the antipodal coils 650, 656 are being energized by the controller 632 with drive signals 634, which causes a pitch or yaw movement defined by the angle, θ, which may be −20 degrees of pitch or yaw.

In some embodiments, therefore, swiveling the eyeball is achieved with little or no net translational force being applied to the eyeball or inner sphere. A magnet/coil configuration is used that is symmetrical that acts to exert balanced forces around the center of the eyeball or inner sphere so that only (or at least mainly) rotational torques are applied during eyeball/inner sphere pitch and/or yaw (or combinations thereof) movement. In this manner, friction by the eyeball or inner sphere rubbing against the inner surfaces of the outer shell is eliminated because the opposite, equal magnitude driving forces combined with neutral buoyancy provided by the suspension liquid nearly prevent the inner sphere or eyeball from contacting the outer shell during normal operations of the eye assembly.

In some embodiments, there are four small permanent magnets mounted at the North and South poles and at the extreme left and rights sides of the inner sphere on a great circle of this sphere, and the magnets are installed so their poles align across the sphere (are arranged on antipodal points of the inner sphere). These internal or inner sphere-mounted magnets are bracketed fore and aft by electromagnetic coils on the outer shell as shown in the figures. Restoring magnets (e.g., contoured and relatively weak rubberized magnet strips or the like) are applied over each pair of these coils on the outer shell. These restoring magnets may be empirically shaped to generate a quasi-uniform magnetic field across the eye ball assembly providing a restoring magnetic force for the permanent magnets on/in the inner sphere, so that its rest position is centered between the drive electromagnetic coils. The controller (such as controller 632) may be a relatively simple design such as an opamp voltage follower circuit used with power source (such as power source 636) to apply a drive voltage (such as signals 634) and, therefore, current to alternating pairs (or antipodal pairs) of the drive coils at the top/bottom and/or left/right sides of the eye assembly. In some cases, a user input device such as an analog joy stick may be used to allow users/operators to quickly move the eyeball or inner sphere by providing and/or modifying the input drive signals via the controller.

One advantage of embodiments of the described eye assemblies is that open loop control may be acceptable for use in all but the most stringent applications because the position of the eyeball or inner sphere may be caused to directly track the strength of the driving magnetic field. Control is simplified, and there is no need for feedback on the eye position. The eyeball or inner sphere may be driven to plus/minus 20 degrees yaw and tilt/pitch such as by approximately plus/minus 200 milliAmps of coil current per axis, and the drive current at the neutral position is 0 milliAmps due to the no-power restoring magnets. The dynamic drive current can easily be reduced by increasing the number of windings on the drive coils (e.g., if 100 turns of 0.13 mm wire for an approximate 4.5 ohm coil is used, increasing the number of turns likely will reduce the drive current used). Drive coils that wrap completely around the outer shell may be useful in some applications such as to free up more of the front-of-eye view.

In one prototyped embodiment, the eye assembly's maximum saccade rate was measured using an NAC Image Technology, Model 512SC high-speed video camera set at the 100 frame/second rate. Frames were counted during plus/minus 20 degree excursions of the eyeball/inner sphere while driving it with an approximate square wave of current on each axis. With a 400 mA peak coil current drive, the peak saccade speeds measured were approximately 500 degrees/second, which exceeds the human eye speed of approximately 200 degrees/second for small excursions. The speed/power tradeoff may be optimized for the eye assembly and can be tailored, for example, by varying the viscosity of the suspension liquid and/or by modifying the coil or drive mechanism structures. For example, adding small amounts of water to the suspension liquid lowers its viscosity and supports higher sustained speeds at a given current.

While eye assemblies described herein may be particularly well suited for animatronic uses, the eye assemblies may be used in many other settings such as novelties and toys and also for medical or prosthetic applications. This may involve using the above described configurations such as with the drive coils mounted on the outer shell that is used as part of the lens assembly and to contain/hold a volume of liquid and the inner sphere or eyeball. In some prosthetic (or other product/service) applications, though, it may be more useful or desirable to utilize remote coils or other external drive mechanisms spaced apart from the outer shell and further away from the rotated/driven inner sphere.

Figure 7:
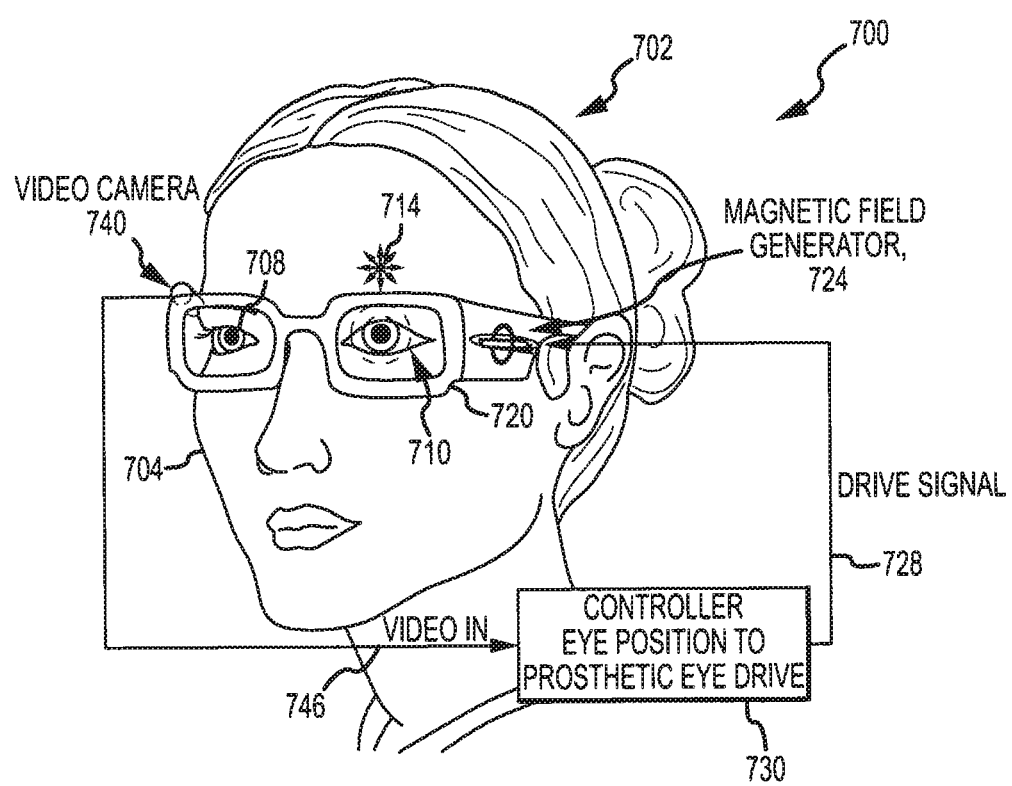
FIG. 7 illustrates a prosthetic eye assembly of one embodiment useful for providing eye rotation with a remote magnetic field generator.

For example, FIG. 7 illustrates a prosthetic eye assembly 700 in which the rotary part of the assemblies described above are provided to a user/recipient 702 as a human-eye prosthesis 710 that is positioned within the eye socket of the recipient's head/skull 704. The eye prosthesis may include the outer shell, suspension fluid, and the eyeball/inner sphere as described above. The eye prosthesis 710 is well suited to this application 700 as its outer shell does not rotate but, instead, only appears to due to the magnification of the inner sphere, which is rotatable using remote magnetic fields. The eye prosthesis 710 may be manufactured in the form of a smooth but rugged, hermetically-sealed, inert ball that may be placed in the eye socket of the recipient's head 704 with no need to worry about rotational friction or rubbing against sensitive human tissue. Since the eye 710 is magnetically driven or steered, the drive force may be exerted from outside the skull to cause the rotation of the eyeball in prosthesis 710 as shown at 714 such as to move similarly or track movement of active/functioning eye 708.

As shown in FIG. 7, the assembly 700 includes a pair of eyeglasses 720 or another support may be provided for the components of assembly 700. A magnetic field generator 724 is mounted in or on the bow of the eyeglasses frame 720 such as adjacent the eye prosthesis 710 to selectively generate a magnetic field to move 714 the eyeball or inner sphere that is suspended in liquid in an outer shell in eye 710. To track movement of eye 708, the assembly may include a video camera 740 that provides video data or video input 746 to a controller 730 that operates to provide drive signals 728 to the magnetic field generator 724 such as based on the eye position of eye 708.

As shown, the drive 724 for this human-embedded eye 710 may come from a modified pair of eyeglasses 720. The glasses 720 may contain either a compact set of electromagnet coils to rotate the eyeball of prosthesis 710 or one or more permanent magnets that may be driven by a miniature servo system or the like. It may be useful in some cases to provide a magnetic rotating system, such as like the fluid-suspended electromagnetic spherical drive described herein that is used to indirectly operate 714 the eyeball or inner sphere in the prosthesis 710. The drive or magnetic field generator 724 may be devoted to rotating a permanent magnet outside the skull 704 that in turn would drive the eyeball or inner sphere in the prosthesis 710. In each arrangement of drive 724, the human-embedded eye or prosthetic eye 710 may follow the motion of the external magnetic field provided by generator 724.

In some cases, the assembly 700 is adapted to provide eye tracking of the eyeball or inner sphere of the prosthetic eye 710 to the other, still functioning human eye 708. This may be achieved using video signals, optical signals, and/or electrooculography signals (e.g., tracking the small voltages generated around the human eye socket when the eyeball 708 rotates), with a video camera 740 combined with a controller 730 that uses eye-tracking software to generate a drive signal 728 being shown in assembly 700. In any of these tracking implementations, the electromagnetic prosthetic eye 710 may be operated to move the eyeball or inner sphere to match the gaze direction of the human eye 708 so as to provide a realistic prosthetic with regard to appearance and movement/rotation 714.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. As will be appreciated from the above description, the eye assembly provides eyeballs or inner spheres that have a full range of movement (or a range similar to the eye being simulated), and the whole mechanism is hardly bigger than the eyeball itself such that it can be installed in existing animatronic heads without even having to remove the old/existing actuators. The eye assembly has no moving parts outside the container or shell making it easy for use in retrofitting other eyes or to use in other settings such as a prosthetic or in compact robots, toys, or the like. The drive has low power requirements and consumption making it a useful eye assembly for untethered implementations and use of battery power.

Further, the number of magnetic drives or drive mechanisms and corresponding inner sphere-mounted magnetic elements that are utilized may be varied to practice the eye assemblies described herein. For example, it may be useful to use a number other than 4 such as to use 3 drive mechanisms and 3 corresponding inner sphere-mounted magnetic elements that may be provided at 120-degree intervals along a great circle of the inner sphere and the outer shell (e.g., perpendicular to the line of sight of the eye or about/near the equator of the outer shell with the inner sphere being aligned due to operation of the coils and/or a set of restoring magnets). In other cases, more than 4 drive mechanisms and inner sphere-mounted magnetic elements may be utilized to suit a particular application.

Additionally, the camera was shown typically mounted external to the inner sphere or eyeball, which was typically formed to be solid. In other cases, a non-solid eyeball or inner sphere may be utilized. In such cases, the camera may still be positioned external to the inner sphere or its lens may be positioned within the hollow inner sphere (e.g., as a payload of the body of the eye assembly that basically acts as a spherical motor that may have any number of payloads such as cameras (e.g., a wired device or more preferably wireless device (which may include power and video transfer in a wireless manner), lights, and the like)).

In some embodiments, a means for tracking movement of a functioning eye is provided in the eye assembly apparatus, as is discussed above, and this may involve use of electrooculography (EOC) for eye tracking (and EOC may even be used for the non-functioning eye in some cases). The tracking means may be wearable, implantable, and/or the like. For example, embodiments may be provided by implanting the control and/or the EM drivers. In other words, although wearable tracking devices are specifically shown in the figures, these may be replaced or supplemented with implantable tracking devices in some applications.

We claim:

1. A prosthetic eye assembly, comprising:
   a spherical, hollow outer shell for positioning within a human eye socket of a prosthesis recipient, wherein the outer shell includes a front portion transmitting light with a first index of refraction;
   a suspension liquid contained within the outer shell, the suspension liquid transmitting light with a second index of refraction substantially matching the first index of refraction;
   a spherical body suspended within the liquid; and
   a magnetic drive assembly comprising a set of magnetic elements provided on a great circle of the spherical body and a magnetic field generator positioned a distance apart from the outer shell, wherein the magnetic field generator generates magnetic forces rotating the spherical body.

2. The assembly of claim 1, wherein the set of magnetic elements comprises at least three permanent magnets provided on a great circle of the spherical body.

3. The assembly of claim 2, wherein the suspension liquid fills a space between the spherical body and the outer shell.

4. The assembly of claim 3, wherein the suspension liquid has a specific gravity to provide a neutral buoyancy to the spherical body.

5. The assembly of claim 1, further comprising a controller providing drive signals to the magnetic field generator to drive the spherical body to have yaw and pitch movements tracking movement of a functioning eye of the prosthesis recipient.

6. The assembly of claim 5, further comprising means for tracking the movement of the functioning eye.

7. The assembly of claim 6, further comprising a frame wearable by the prosthesis recipient, wherein the magnetic field generator and the tracking means are mounted in the frame with the magnetic field generator adjacent the spherical body.

8. A prosthetic eye assembly, comprising:
   an outer shell;
   a suspension liquid contained within the outer shell;
   a spherical body suspended within the suspension liquid; and a magnetic drive assembly comprising magnetic elements on or in the spherical body and a magnetic field generator selectively generating magnetic forces interacting with the magnetic elements to position the spherical body within the outer shell, wherein the magnetic elements comprise a plurality of permanent magnets positioned equidistally on a great circle of the spherical body, and wherein the suspension liquid fills a space between the spherical body and the outer shell and the suspension liquid has a specific gravity to provide a neutral buoyancy to the spherical body.

9. The assembly of claim 8, further comprising a controller providing drive signals to the magnetic field generator to drive the spherical body to have yaw and pitch movements tracking movement of a functioning eye of the prosthesis recipient.

10. The assembly of claim 9, further comprising means for tracking the movement of the functioning eye.

11. The assembly of claim 10, further comprising a frame wearable by the prosthesis recipient, wherein the magnetic field generator and tracking means are mounted in the frame with the magnetic field generator adjacent the spherical body.

12. An eye assembly, comprising:
a spherical, hollow outer shell for positioning within an eye socket;
a suspension liquid contained within the outer shell;
a spherical body suspended in the suspension liquid within the outer shell, wherein the suspension liquid has a specific gravity to provide a neutral buoyancy to the spherical body;
a magnetic drive assembly comprising one or more magnetic elements on or in the spherical body and a magnetic field generator generating magnetic forces acting on the magnetic elements for rotating the spherical body;
means for tracking the movement of the functioning eye; and
a frame wearable by the prosthesis recipient, wherein the magnetic field generator and the tracking means are mounted in the frame with the magnetic field generator adjacent the spherical body.

13. The assembly of claim 12, wherein the magnetic elements comprise a plurality of permanent magnets provided on a great circle of the spherical body.

14. The assembly of claim 12, wherein the suspension liquid fills a space between the spherical body and the outer shell.

15. The assembly of claim 12, further comprising a controller providing drive signals to the magnetic field generator to drive the spherical body to have yaw and pitch movements tracking movement of a functioning eye.

\* \* \* \* \*